US005858189A

United States Patent [19]
Williams

[11] Patent Number: 5,858,189
[45] Date of Patent: Jan. 12, 1999

[54] SAMPLE HOLDER AND METHOD FOR AUTOMATED HIGH THROUGHPUT ELECTROPHORESIS

[75] Inventor: John Gregory Kelly Williams, Ankeny, Iowa

[73] Assignee: E.I. du Pont de Nemours and Company, Wilmington, Del.

[21] Appl. No.: 785,911

[22] Filed: Jan. 21, 1997

Related U.S. Application Data

[63] Continuation of Ser. No. 183,558, Jan. 19, 1994, abandoned.

[51] Int. Cl.$^6$ .................................................. G01N 27/26
[52] U.S. Cl. ........................ 204/456; 204/606; 204/616; 204/466
[58] Field of Search .................................. 204/456, 466, 204/465, 467, 606, 616, 618, 619, 620

[56] References Cited

U.S. PATENT DOCUMENTS

| | | | |
|---|---|---|---|
| 3,879,280 | 4/1975 | Peterson et al. | 204/299 |
| 3,932,265 | 1/1976 | Hoefer | 204/299 |
| 4,061,561 | 12/1977 | Fletcher et al. | 204/299 R |
| 4,199,428 | 4/1980 | Hayashi et al. | 204/299 R |
| 4,294,684 | 10/1981 | Serwer | 204/299 |
| 4,391,689 | 7/1983 | Golias | 204/180 G |
| 4,578,169 | 3/1986 | Vicario et al. | 204/299 R |
| 4,795,541 | 1/1989 | Hurd et al. | 204/299 |
| 4,861,411 | 8/1989 | Tezuka | 156/344 |
| 4,883,577 | 11/1989 | Sugimoto et al. | 204/299 |
| 4,909,918 | 3/1990 | Bambeck, et al. | 204/299 |
| 4,909,977 | 3/1990 | Hurd et al. | 264/261 |
| 5,217,591 | 6/1993 | Gombocz et al. | 204/299 R |
| 5,284,565 | 2/1994 | Chu et al. | 204/299 R |
| 5,344,534 | 9/1994 | Danziger | 204/182.8 |

OTHER PUBLICATIONS

R. Wiggins, *Anal. Biochem.*, 126(2), 422–424, 1982. month unavailable.

K. Atland et al., *Electrophoresis*, 9(9), 485–488, 1988. month unavailable.

D. Gersten et al., *Electrophoresis*, 3(4), 231–232, 1982. month unavailable.

K. Nakamura et al., *Anal. Biochem.*, 195(2), 269–272, 1991. month unavailable.

V. Neuhoff et al., *Electrophoresis*, 7(1), 56–57, 1986. month unavailble.

L. Orban et al., *J. Biochem. Biophys. Methods*, 9(1), 105–120, 1989. month unavailable.

G. Bellomy et al., *Biotechniques*, 7(1), 16, 19–21, 1989. Sep. 1985 (Publ).

L. Orban et al., *Electrophoresis*, 10(10), 726–729, 1989. Sep. 1985, (publ).

T. Marshall et al., *Electrophoresis*, 10(1), 63–65, 1989. Sep. 1985 (publ).

R. Clements, *Cereal Chem.*, 65(2), 150–152, 1988. Sep. 1985 (publ).

C. Wrigley, *Adv. Electrophor. Tech. Protein Invest. Clin. Diagn.*, [Aust. Workshop Adv. Protein Electrophor. Tech.], 1st Meeting Date 1984, pp. 58–63, 1985. Sep. 1985 (publ).

A. Rhalem et al., *Electrophoresis*, 6(11), 564–566, 1985. month unavailable.

W. Black et al., *Anal. Biochem.*, 138(1), 210–216, 1984. month unavailable.

P. Tanner et al., *Biokhim. i Populyatsion. Genet. Ryb*, L. From: Ref. Zh., Biol. Khim., 1980, Abstr. No. 18F192.

G. Bradley et al., *Tech. Bull. Regist. Med. Technol.*, 38(3), 64–66, 1968. month unavailble.

J. States et al., *Biotechniques*, 11(1), 46–48, 1991. month unavailable.

R. Wilson et al., *BioTtechniques*, 6(8), 776–787, 1988. month unavailable.

*Primary Examiner*—Kathryn L. Gorgos
*Assistant Examiner*—Alex Noguerda

[57] ABSTRACT

A sample holder for receiving, containing and storing multiple samples for delivery to an electrophoretic gel; and a method of preparing a gel for electrophoresis such that samples are first loaded onto a separate holder which can then be positioned at an edge of a gel bed surface while the electrophoretic gel is poured, whereby after solidifcation thereof the sample holder is removed leaving the samples adhered in a position for delivery to the electrophoretic gel after current is applied to the system.

16 Claims, 7 Drawing Sheets

SAMPLE HOLDER AND METHOD FOR AUTOMATED HIGH THROUGHPUT ELECTROPHORESIS

This application is a continuation of U.S. application Ser. No. 08/183,558, filed Jan. 19, 1994, which is now abandoned.

FIELD OF THE INVENTION

The present invention relates to a sample holder and a highly efficient method of loading a sample for gel electrophoresis.

BACKGROUND OF THE INVENTION

Electrophoresis is a process in which macromolecules are separated on the basis of their charge-to-mass ratios by forcing them to move through a carrier medium, such as a porous gel, by means of a voltage gradient applied across the gel. Molecules having uniform charge-to-mass ratios, such as DNA and RNA, are differentiated on the basis of size.

Gel electrophoresis is a technique frequently used for separation with proteins and nucleic acids. In traditional methodology, a gel is cast as a thin slab between plates (for vertical runs) or alternatively poured and cast onto a flat bed (for horizontal runs) and positioned between buffer/electrode compartments in an electrophoresis apparatus. An appropriate buffer solution is added to the buffer/electrode compartments of the apparatus, and a small amount of sample solution is then carefully pipetted into precast notches on top of the gel. Usually glycerol and a "tracking" dye are contained within the notches, or added to the sample solution. An electric current is then applied across the gel until the tracking dye band has migrated through the length of the slab. The electric current is discontinued, and the gel is removed from the apparatus. At this point the gel is analyzed to determine the relative migration of the sample molecules. The gel may be stained, for example, with a dye that binds to proteins or nucleic acids, and the gel may then be dried or preserved, or a photograph taken, thus rendering a permanent visual record of the size distribution of the molecules in the original sample solution.

Electrophoresis gels typically are cast to accommodate multiple samples in an elongated gel slab. The gel slab is usually formed by inserting a comb device into nonsolidified gel medium. Usually the comb device has a plurality of equally spaced protrusions which resemble the teeth of a hair comb. The gel medium is then allowed to "gel", or harden, and the comb is removed resulting in the formation of sample-receiving wells within the upper portion of the gel slab.

Gel electrophoresis run in the conventional manner, as described above, is inherently inefficient. Typically, an operator must load the wells of the gel slab manually with a hand-held pipette. Samples must then be run immediately to prevent diffusion of the samples into the buffer. Therefore, loaded samples may not be stored, and thus, an operator must run tests immediately rather than when convenient. Also, the number of samples per gel made in the conventional manner is limited in order to provide a target well large enough to be loaded accurately.

Roger C. Wiggins in an article entitled "Agarose Drop Method for Loading Thin Polyacrylamide Gels", Analytical Biochemistry 126, pp. 422–424 (1982), describes a technique for gel electrophoresis where molten agarose is added to a crystalline sample and allowed to solidify. Each sample is then separated by cutting the backing on which it is placed, and the sample is slid onto a glass back plate of a horizontal gel mold and placed in contact with a polymerized stacking gel. The disadvantages of the Wiggins' technique are that the process is more labor intensive than simple well loading, and only has utility for very small samples sizes. The technology does not lend itself to automation thus limiting the number of samples that could be analyzed in a period of time. The technology is also limited in that the resulting band profile is a function of the size and shape of the sample drop, leading to lane patterns that are not reproducible.

Automation has been attempted in efforts to increase sample throughput in electrophoresis processes. For example, in a development program for automating gel loading at Beckman Instruments, Inc., a programmable pipetting machine, the Biomek Workstation, has been developed. Each individual precast gel is mounted on the Biomek, electrophoresis samples are loaded by the instrument, and then the gel is removed. The disadvantage of this system is that only a single gel can be loaded at a time. Also, because of the limits of pipetting accuracy, sample loading wells have to be quite large to be accessed accurately by the robotic arm. It is difficult to accurately deliver the Biomek pipet into a thin sample well, and thin wells are desirable because they determine band resolution in the gel. If the well is made thick enough to allow accurate pipetting, significant band resolution is lost. Another disadvantage of the Biomek method is that only one gel at a time can be loaded. Because of the above problems, and the lack of ease of operation, the Biomek method of automated gel loading has not been adapted widely by the research community.

A system for automated gel loading also eliminates pipetting error which occurs when samples are switched or mixed up during hand-held loading. Thus, multiple robotic pipetting not only hastens the loading procedure but also protects against application of wrong sample sequences.

In designing the sample holder and automatable gel loading process of the instant invention, Applicant recognized several constraints. First, the efficiency of an automated process would be improved by increasing the number of samples which could be loaded simultaneously on a sample loading machine. However, when the size and spacing of sample wells is decreased in an effort to provide a higher density of wells per gel, the pipetting machine must be increasingly more precise in order to successfully deliver samples to the smaller wells. Hence, one problem to overcome is how to increase the number of sample wells per gel while maintaining a target well size that can be hit by a robot arm on the pipetting machine. A second related constraint involves trying to maintain a very thin well in the dimension of the direction of sample electrophoresis to maintain high band resolution. A third constraint involves the need to design a sample loading system whereby the automated sample delivery device can efficiently load samples for more than one gel slab at a time. A fourth constraint is the need to provide a system of loading samples wherein the loaded samples may be stored for a length of time before they are electrophoresed through the gel. Sample diffusion and integrity must be controlled during storage.

Hence, a better, more efficient method of automatable gel electrophoresis is needed. It is an object of the present invention to solve the problems associated with conventional gel electrophoresis by providing a method of loading samples into a separate sample holder unconnected from the gel slab, wherein the samples are allowed to gel within individual wells within the sample holder and can therein be stored until electrophoresis. Another unique and beneficial feature of Applicant's gel loading system is that sample aliquots are delivered to the sample well chamber from a position parallel and not perpendicular to the electrophoretic axis, in other words, into the front of the sample well chamber rather than into the "top" of the sample well chamber, relative to the direction of the electrophoretic current as the well is viewed when in position for electrophoresis. Thus, the surface area available for delivery of the sample to the well is greatly increased compared to traditional horizontal loading schemes, where the sample is loaded into the top portion of the well chamber from an angle perpendicular to the electrophoretic axis.

SUMMARY OF THE INVENTION

This invention provides a sample holder for receiving a pre-solidified electrophoretic sample and for containing said electrophoretic gel sample after solidification for delivery to an electrophoretic gel, said sample holder comprising a plate having at least one sample well formed in the front face thereof.

This invention also provides a process for loading an electrophoretic gel sample onto an electrophoretic gel, comprising the steps of:

(a) delivering the sample and a molten first gel medium to a sample well formed within a sample holder, said sample holder comprising a plate having at least one sample well formed in the front face thereof;

(b) allowing the molten first gel medium to solidify within the sample well;

(c) positioning said sample holder in an electrophoretic chamber in a manner sufficient to place the solidified first gel medium contained in the sample well in proximity to a bed within the electrophoretic chamber;

(d) adding a molten second gel medium onto the bed within the electrophoretic chamber whereby the molten second gel medium is contacted with the solidifed first gel medium contained in the sample well recited in step (c); and (e) allowing the molten second gel medium to solidify in the bed.

In the process recited above, the sample holder may remain in place if made of an electrically conductive material, or is removed if made of other non-conductive material. In either case, the solidified sample and first gel medium remain adhered to the solidified second gel medium in a position sufficient to deliver the sample thereto when electric current is delivered across the gel medium.

This invention also provides a system for performing gel electrophoresis, comprising:

(a) an electrophoretic chamber having an electrophoretic bed, said bed being positioned between two buffer/ electrode compartments and extending from one side wall of the electrophoretic chamber to an opposite side wall of the electrophoretic chamber; and (b) a sample holder comprising a plate having at least one sample well formed in the front face thereof.

BRIEF DESCRIPTION OF THE DRAWINGS

The accompanying drawings, which are incorporated in and constitute a part of the specification, illustrate the presently preferred embodiments of the invention and, together with the general description given above and the detailed description of the preferred embodiments given below, serve to explain the principles of the invention.

DETAILED DESCRIPTION OF THE PREFERRED EMBODIMENTS

Reference will now be made in detail to the present preferred embodiments of the invention as illustrated in the accompanying drawings.

The present invention provides a sample holder for receiving a pre-solidified electrophoretic sample and for containing the electrophoretic gel sample after solidification for delivery to an electrophoretic gel. The pre-solidified sample may comprise protein, nucleic acids or other molecules, which are mixed with a molten or nonsolidified gel medium prior to loading into the sample holder, or alternatively, the sample and gel medium may be mixed within a sample well within the sample holder.

Figure 1:
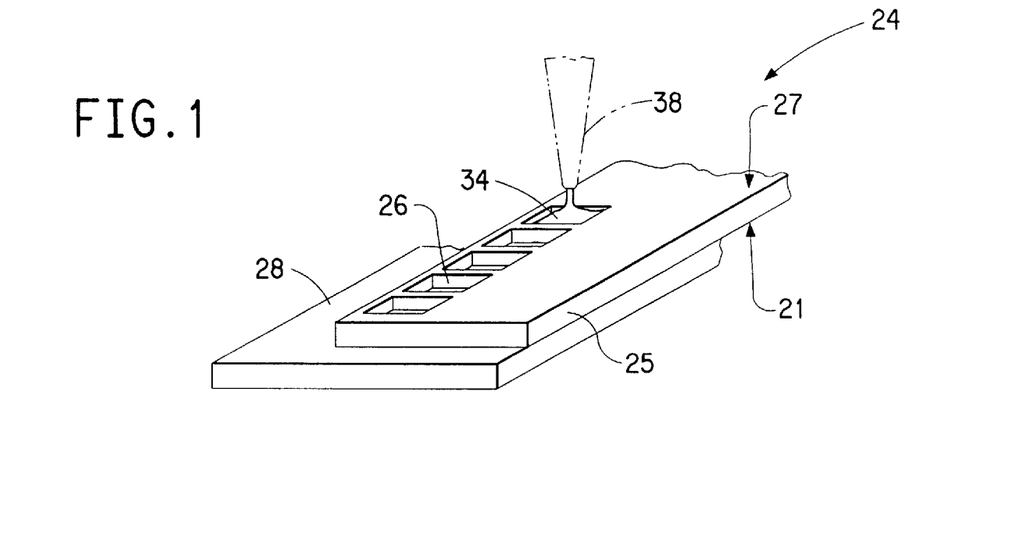
FIG. 1 is a perspective view of the preferred sample holder according to the present invention showing a backing attached to a back face of the plate.
Figure 2:
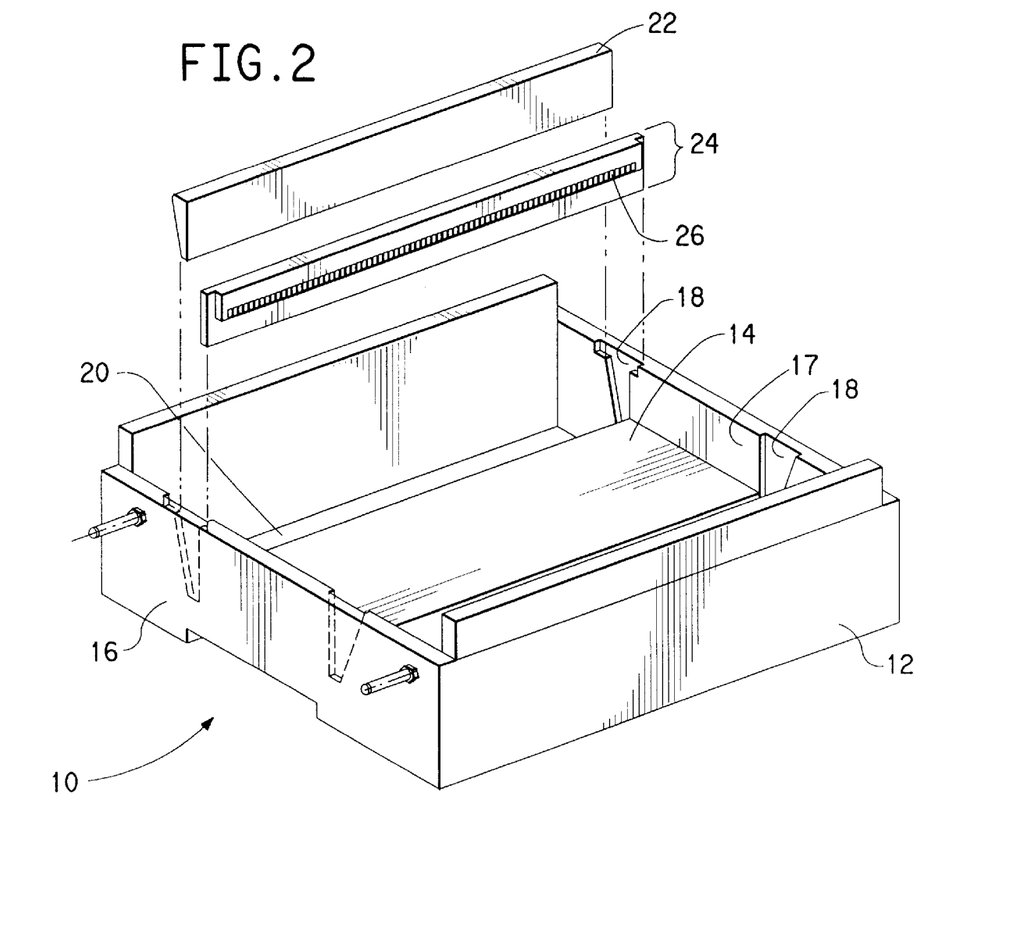
FIG. 2 is a perspective view of the disassembled elements of the electrophoresis system according to the present invention showing an electrophoretic chamber, a sample holder and a wedge.
Figure 5:
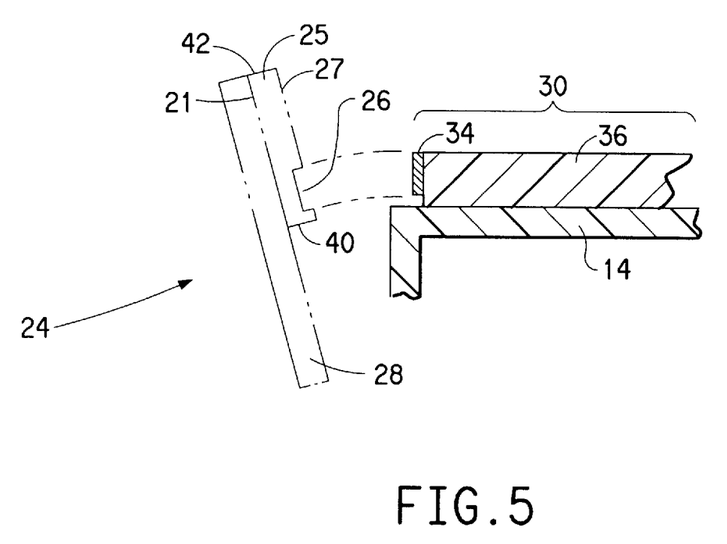
FIG. 5 is a cross-sectional view showing optional removal of the sample holder to yield a loaded electrophoretic gel comprising a solidified electrophoretic second gel medium with a sample in a first gel medium adhered thereto, whereby the first gel medium is inset from the edge of the electrophoretic bed within the electrophoretic chamber.

A sample holder is shown at 24 in FIG. 1 and FIG. 2. Sample holder 24 comprises a plate 25. The plate 25 is, preferably, substantially planar and rectangular as shown in FIGS. 1 and 2. As shown in FIG. 5, pate 25 extends in a first plane and has a front face 27, a back face 21, a first side face 40 and a second side face 42. Representative dimensions of plate 25 are as follows: length, 24 cm; width, 2.5 cm; height, 0.6 cm. These dimensions may vary depending on the size of an electrophoretic unit.

As shown in FIGS. 1 and 2, at least one sample well 26 is formed in the front face 27 of plate 25. The at least one sample well 26 extends generally perpendicular to the plane of plate 25 and proximate first side face 40. Preferably, a plurality of sample wells are formed in front face 27 of plate 25. More preferably, a plurality of equally spaced sample wells 26 are longitudinally aligned along front face 27 of plate 25. The number of sample wells 26 formed within plate 25 and dimensions of the sample wells 26 would depend on the size of the sample holder 24 and electrophoretic gel desired. A preferred number of sample wells 26 would be a multiple of the number of pipettes on a robotic pipetting device plus at least one extra sample well for loading of molecular weight marker molecules. A preferred number of sample wells 26 within sample holder 24 of 24 cm×2.5 cm×0.6 cm dimension is 76, and representative dimensions for sample well 26 formed in a sample holder of such dimension are as follows: length, 2.5 mm; width, 4 mm; and depth, 1 mm. Sample wells of these dimensions could be filled with about up to 25 $\mu$l of sample and gel medium.

Figure 3:
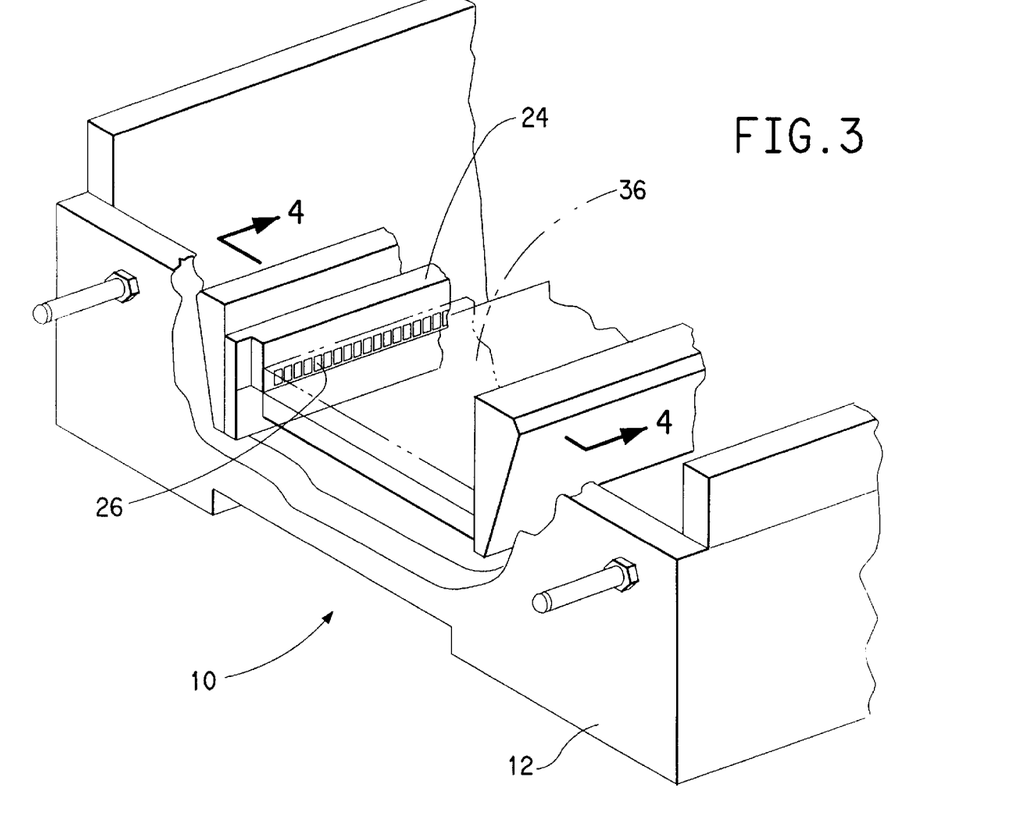
FIG. 3 is a side perspective view of the electrophoresis unit of FIG. 2 according to the present invention showing the sample holder and a pair of wedges positioned in the electrophoretic chamber.
Figure 4:
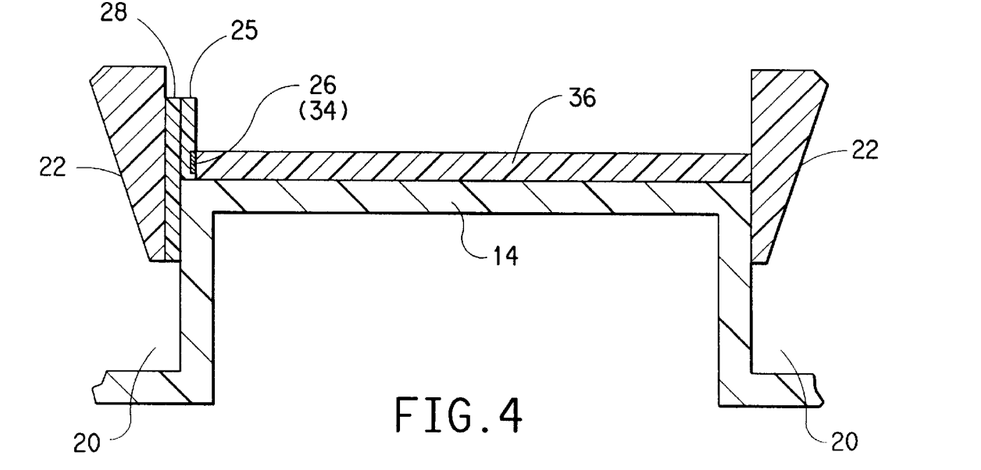
FIG. 4 is a cross-sectional view of the electrophoresis unit of FIG. 3 showing the sample holder positioned sufficient to place the sample wells in proximity to the edge of the bed.

Preferably, sample holder 24 further comprises a backing 28 attached to the back face 21 of plate 25, whereby backing 28 facilitates placement of sample holder 24 within an electrophoretic chamber 12 in proximity to an electrophoretic gel bed 14 as shown in FIGS. 2–4. As shown in FIG. 5, backing 28 is disposed in contact with plate 25 and extends in a second plane generally parallel to the first plane of plate 25 and has a portion extending beyond first side face 40 of plate 25. Backing 28 serves to position sample well 26 in holder 24 over bed 14 as may be seen in FIGS. 3 and 4. The backing 28 embodied herein has been designed to extend in a downward vertical direction from the bottom of plate 25 when sample holder 24 is oriented for delivery of sample to the electrophoretic gel within a horizontal electrophoretic unit whereby backing 28 holds plate 25 in a position inset from the edge and over the top surface of electrophoretic gel bed 14 contained in a horizontal electrophoretic unit (see FIG. 2). Preferably, plate 25 covers approximately ⅛ to ½ of the longitudinal length of one of the surfaces of backing 28, and sample wells 26 are disposed along a longitudinal edge of plate 25 in such a manner to bring sample wells 26 in proximity to the surface of bed 14 when sample holder 24 is in position for an electrophoresis run. Preferably, plate 25 is sufficiently deep such that sample well 26 is inset from the edge and over bed 14 to a distance about 3 to about 50 mm. In a preferred embodiment plate 25 and backing 28 are formed as one piece.

For electrophoretic systems wherein sample holder 24 is to be removed from chamber 12 prior to electrophoresis, sample holder 24 should be made of a material which facilitates removal (see FIG. 5) of sample holder 24 after solidification of electrophoretic gel 36, such that the adherence formed between the solidified sample and first gel medium in sample well 26 and the second electrophoretic gel medium 36 is not broken. Sample holder 24 can be machined, stamped out or molded, for example, from a plastic, such as Lucite® or nylon, with Lucite® being preferred. Sample holder 24 may also be made from an electrically conductive material that would allow the electrophoretic current to pass through it, making it unnecessary to remove the sample holder 24 prior to passing the voltage through the system with the conductivity of the sample holder being close to that of the electrophoretic gel. Examples of electrically conductive material are plastic resins combined with conductive fillers, such as high strength metal fibers, metal-flake fillers, metallized mica platelets, low aspect-ratio/low density fillers and carbonaceous fibers. Numbers, letters, codes or the like may also be machined, stamped or molded into sample holder 24 for identification and record-keeping purposes.

The present invention also provides for a process for loading an electrophoretic gel sample on an electrophoretic gel, comprising the steps of:

(a) delivering the sample and a molten first gel medium to a sample well formed within a sample holder, said sample holder comprising a plate having at least one sample well formed in the front face thereof;

(b) allowing the molten first gel medium to solidify within the sample well;

(c) positioning said sample holder in an electrophoretic chamber in a manner sufficient to place the solidified first gel medium contained in the sample well in proximity to a bed within the electrophoretic chamber;

(d) adding a molten second gel medium onto the bed within the electrophoretic chamber whereby the molten second gel medium is contacted with the solidifed first gel medium contained in the sample well recited in step (c); and (e) allowing the molten second gel medium to solidify in the bed.

In the process recited above, the sample holder may remain in place if made of an electrically conductive material, or is removed if made of other non-conductive material. In either case, the solidified sample and first gel medium remain adhered to the solidified second gel medium, whereby the sample contained in the solidified first gel medium migrates to the solidified second gel medium when electric current is applied across the gel medium.

Although sample well 26 may be loaded manually with a hand-held pipette 38, as shown in FIG. 1, for increased throughput, loading may also be accomplished using automatic means, for example, with the use of a programmable or robotic pipetting device, such as a Beckman Biomek Workstation from Beckman Instruments, Inc., Palo Alto, Calif. The pipette system found on the Biomek Workstation may be connected to a supply of molten or nonsolified first gel medium 34 and then mixed with individual samples for automatic delivery to one or more sample holders which are positioned on the loading surface of the Biomek unit. Other means of automated or manual mixing and delivery of samples to the first gel medium are contemplated. The sample may be mixed with the first gel medium and then loaded to the sample well; or the first gel medium may be added to the sample well and then the sample added; or vice versa.

Examples of common gel-forming media suitable for use in the present invention include agarose, polysaccharide, polyacrylamide, water-soluble, cross-linked polymer and starch. The term "molten" as used within the context of this invention refers to the liquid or nonsolid state of the gel. For example, when the invention practices agarose as the first gel medium to be mixed with the sample, the "molten" state is achieved by heating the gel medium. Chemical means may also be used to solidify other gel mediums. The invention may be practiced using acrylamide as the separating medium, for example, by first mixing the sample with molten agarose in the sample well, allowing the samples to solidify, and delivering the samples to a cast acrylamide gel to which a top layer of molten agarose has been added. Agarose is preferred for both the first and second gel medium in the present invention. When agarose is used as the gel medium, the percent of agarose to be mixed with sample ranges from about 0.35% to about 0.7%. The preferred range of agarose is in the range of 0.5%.

The mixture of sample and molten first gel medium 34 may be deposited into sample well 26 as shown in FIG. 1. Because sample holder 24 is loaded in a flat orientation, small sample wells 26 can be spaced at high density along the sample holder 24 while still providing large target surface area for sample loading. Preferably, the number of sample wells 26 is a multiple of the number of pipettes found on the robotic pipetting device plus at least one additional well on at least one end of front face 27.

Many sample holders 24 may be mounted on the robotic pipetting device simultaneously, thus increasing the number of sample wells 26 that can be filled during a certain time period. An obvious advantage of the present invention is that since the sample holder is loaded independently of the separating gel, there is no need to accommodate and handle the large separating gel during the sample loading process.

The process for loading a sample onto a gel may further comprise after step (b), storing the sample holder containing the solidified sample and first gel medium for a period of time prior to performing step (c). The loaded sample holder 24 may be stored at temperatures ranging from about 4° C. to about 23° C. until it is convenient to perform the electrophoresis run provided that care is taken to prevent the sample from drying out or degrading. A sticky tape may be used to cover the solidified samples in the sample holder to prevent evaporation.

As shown disassembled in FIG. 2 and assembled in FIG. 3, a typical electrophoresis unit used for electrophoresis according to the present invention comprises an electrophoretic chamber 12, sample holder 24, and means for holding the sample holder in place 22, 18 and 14. The electrophoretic chamber 12 is formed such that a portion of its base is raised to form a bed 14 extending from one inner surface 17 of side wall 16 of the electrophoretic chamber 12 to an opposite inner surface 17 of side wall 16 such that bed 14 is positioned between two buffer/electrode compartments 20. Preferably, the inner surface 17 of each side wall 16 has at least one vertical through-slot 18 formed therein perpendicular to an edge of bed 14. The through-slots 18 accommodate insertion of wedge 22 and sample holder 24.

Ultraviolet (UV) transparent glass may be used for the raised portion of the base of electrophoretic chamber 12 which forms bed 14. Use of this type of material facilitates visualizing and photographing the results of the electrophoresis.

Given sufficient time the mixture of sample and first molten gel medium 34 "gels" or solidifies by cooling, or by other solidification means, such as chemical means. The sample holder 24 is then turned up on edge as shown in FIGS. 2, 3 and 4 and slid into vertical through-slots 18 on the inside surface 17 of side walls 16 and is thus mounted at one edge of bed 14. In a preferred embodiment of the present invention, sample well 26, and thus the mixture of sample and first gel medium, are inset from the edge of the bed to a position over the top of the surface of bed 14. Most preferably, sample well 26 is inset from the edge of bed 14 entirely over the surface of bed 14 to a distance about 3 mm to about 50 mm from the edge of bed 14 as shown in FIG. 5. This positioning may be facilitated by using a preferred sample holder 24 comprising a backing 28 and plate 25 with backing 28 extending beyond plate 25 in at least a downward vertical direction when sample holder 24 is positioned for delivery of the sample to the electrophoretic gel.

Means for holding the sample holder in place may comprise, for example, a clamp, a wedge, a pin, or the sample holder may be manually held by an operator. Preferably, a wedge 22 is positioned in vertical through-slots 18 such that sample holder 24 is positioned between one edge of bed 14 and wedge 22 (see FIGS. 2 and 3). Wedge 22 acts to hold sample holder 24 in direct contact against one edge of bed 14 sufficent to allow contact of the first gel medium 34 to the second electrophoretic gel medium 36, and thereby the delivery of the sample to electrophoretic gel 36 as shown in FIGS. 3 and 4. Preferably, there are two wedges 22, the second one fitting into vertical through-slots 18 at the opposite edge of bed 14 as also seen in FIGS. 3 and 4. The second wedge 22 together with sample holder 24, inner side walls 17 and the top surface of bed 14 define the area within which electrophoretic gel 36 is formed as is shown in FIGS. 3 and 4. Wedge 22 may be machined, stamped out, or molded out of plastic such as Lucite® or nylon. The wedge is made of an electrically conductive material, if not removed during electrophoresis with the conductivity of the wedge being close to that of the electrophoretic gel. Examples of electrically conductive material are plastic resins combined with conductive fillers such as high strength metal fibers, metal-flake fillers, metallized mica platelets, low aspect-ratio/low density fillers and carbonaceous fibers.

In the preferred practice of the present invention, electrophoretic bands resulting from an electrophoresis run tend to be sharper when the solidified sample and first gel medium are positioned inset from the edge of bed 14. When the sample gel is not positioned to be inset entirely over bed 14, electric field distortion, possibly from faster migration at the bottom of the sample can occur. This can cause band slanting and significant loss of band resolution, an undesirable result in electrophoresis runs.

After sample holder 24 is placed in position in the electrophoresis unit, an appropriate amount of molten second gel medium is added, for example, by pouring it onto the top surface of bed 14. This molten second gel medium is allowed sufficient time to "gel" or solidify, either by cooling or chemicals means, to form an electrophoretic gel 36. Upon solidification of the second gel medium, sample and first gel medium 34 become fixed in position to deliver sample. This is made possible by electrophoretic gel 36 becoming sufficiently adhered or bonded to the sample and first gel medium 34 contained within sample well 26, that the sample remains attached to electrophoretic gel 36 if sample holder 24 is removed. If sample holder 24 is subsequently removed from electrophoresis unit 10, it is done in such a way that sample and first gel medium 34 slips out of sample well 26 while remaining fixed in position to deliver sample to electrophoretic gel 36, thus forming a loaded electrophoretic gel 32. Sample holder 24 and wedge 22 do not have to be removed if made of conductive material, thus providing a time savings. The loaded electrophoretic gel 32 comprises electrophoretic gel 36 with sample and first gel medium 34 fixed in position to deliver sample to electrophoretic gel 36. Electrophoresis may then proceed by applying current across the gel in a conventional manner.

This invention also provides a system for performing gel electrophoresis, comprising: (a) an electrophoretic chamber having an electrophoretic bed, said bed being positioned between two buffer/electrode compartments and extending from one side wall of the electrophoretic chamber to an opposite side wall of the electrophoretic chamber; and (b) a sample holder comprising a plate having at least one sample well formed in the front face thereof.

The electrophoretic chamber and sample holder are as described above and shown in FIGS. 1–5. Preferably the sample holder comprises a plurality of sample wells.

The system may further comprise an automatic means to deliver multiple electrophoretic samples and molten first gel medium to the sample wells of the sample holder, as described above.

A variety of mediums may be used for the first gel medium, as described above; agarose is preferred. In step (a) the system may further comprise a second gel medium made of agarose contained in the electrophoretic chamber on the surface of the bed.

It is preferred that the present invention be used in horizontal electrophoresis units. However, it is anticipated that vertical electrophoresis units could also be utilized. In vertical embodiments which often use acrylamide as the second gel medium, the top edge of the electrophoretic gel could be covered with a thin layer of molten agarose, and the sample holder which is loaded with solidified agarose and samples is then immediately inserted therein, whereby bonding will then occur between the agarose layer of the electrophoretic gel and the solidified agarose and sample contained in the wells of the sample holder.

The present invention provides a satisfactory way to obtain high sample throughput in gel electrophoresis which is especially desirable in some electrophoresis applications as, for example, in restriction endonucleous fragment length polymorphism (RFLP) analysis, and Random Amplified Polymorphic DNA (RAPD) analysis (U.S. Pat. No. 5,126,239).

EXAMPLE 1

Replicate samples were prepared by mixing 10 $\mu$l of DNA (2 $\mu$g of a 1 kilobase ladder, BRL, Inc. Gaithersberg, Md.) with 10 $\mu$l of molten 1.4% agarose at 48° C. The agarose was either of the standard type (BioRad, Inc.), (see lanes 3, 4, 7 and 8 of FIG. 6), or was of the Low Melting type (BRL, Inc.), (see lanes 1, 2, 5 and 6 of FIG. 6). The final agarose concentration in the mixture was 0.7%. Before the mixtures solidified, 20 $\mu$l of each mixture was pipetted into a sample well of a sample holder, as shown in FIGS. 1 and 2, except that the sample wells were formed in the sample holder backing and there was no sample plate.

The sample holder containing each set of DNA samples was assembled into an electrophoresis unit as shown in FIGS. 2 and 3. A 1% agarose solution was prepared by methods well known in the art and was equilibrated to 48° C. The 1% agarose solution was poured 48° C. onto the horizontal gel bed of the electrophoresis unit and was allowed to solidify at room temperature to form the solidified second gel medium. The wedges were removed and then the sample holder was removed from the gel bed, leaving the samples adhered to the edge of the solidified second gel medium (as shown in FIG. 5).

The first and second set of samples were then separated by cutting the gel slab in half along the direction of electrophoresis. One half of the slab was slid inward, so that the adhered samples in the solidified first gel medium were positioned about 1 inch from the edge of the gel bed (FIG. 6B). The remaining half of the slab was left in place, so that the adhered samples were at the edge of the gel bed (FIG. 6C).

Electrophoresis was performed in 1 X TBE (89 mM Tris pH 8.4, 89 mM boric acid, and 2 mM EDTA disodium salt) at 100 volts for 100 minutes, the separated bands of DNA stained with ethidium bromide, visualized under ultraviolet light and photographed, by methods well known in the art.

Figure 6A:
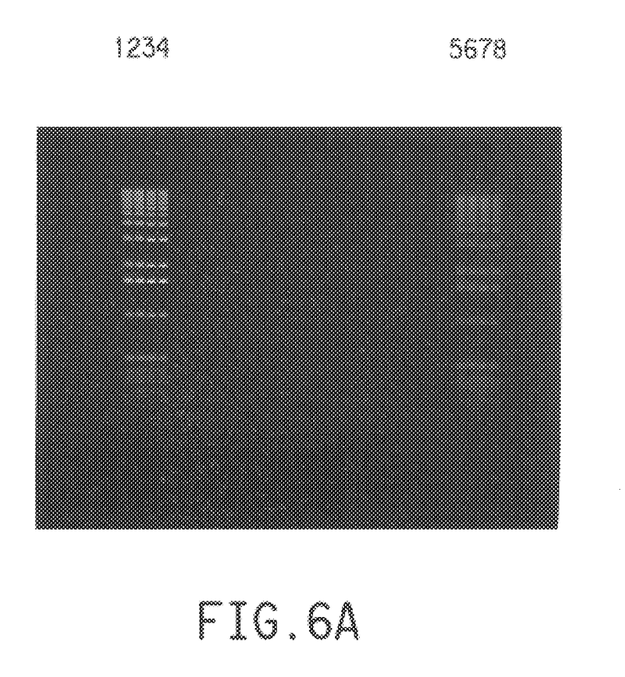
FIG. 6A is a photograph of the electrophoretic gel according to Example 1 of the present invention. Lanes 1–4 show the bands resulting from the 1" inset position of the samples. Lanes 5–8 show the bands resulting from the samples extending beyond the edge of the gel bed. Lanes 1, 2, 5, and 6 contained low melting type agarose. Lanes 3, 4, 7, and 8 contained standard type agarose.
Figure 6B:
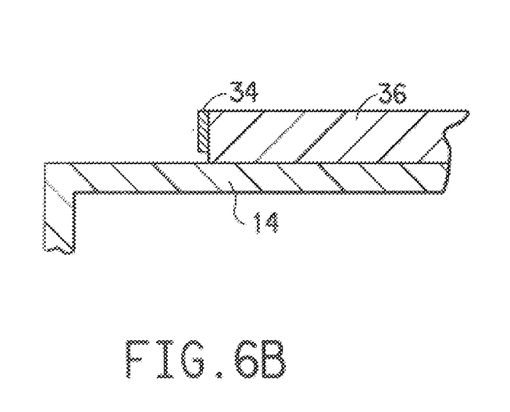
FIG. 6B is a cross-sectional view of the gel bed, the solidified second gel medium and the mixture of sample and first gel medium of Example 1 of the present invention showing the sample inset 1" from the edge of the gel bed.
Figure 6C:
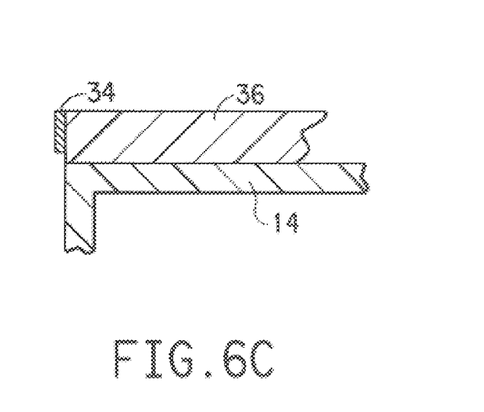
FIG. 6C is a cross-sectional view of the gel bed, the solidified second gel medium and the mixture of sample and first gel medium of Example 1 of the present invention showing the sample positioned beyond the edge of the gel bed.

As shown in FIG. 6A, the DNA samples placed in the sample holder were effectively separated in the solidified second gel medium and show that the DNA samples inset from the edge of the gel bed by 1" (lanes 1–4) were better resolved than the samples allowed to extend beyond the edge of the gel bed (lanes 5–8). When the horizontal gel slab was viewed from the top, bands of DNA were sharper when the samples were inset from the edge of the gel bed. DNA samples that extended beyond the edge of the gel bed ran slanted through the gel. When the gel slab was sliced and the bands viewed from the side, it was apparent that the bands were slanted such that the portion nearest the gel bed (the bottom of the band) had migrated faster than the portion at the gel surface (the top of the band). This effect was greater for the samples adhered at the edge of the gel bed than for the samples inset from the edge of the gel bed. This slanting effect accounts for the sharper band images seen for samples inset from the edge of the gel bed. DNA samples extending beyond the edge of the gel bed experience an uneven electrical field during the early moments of electrophoresis causing the DNA band to migrate in a slanted orientation through the gel. Setting the DNA sample back from the edge of the gel bed places the DNA sample in a more uniform electrical field during the beginning of electrophoresis which results in a higher resolution separation. DNA samples placed in low melting point agarose of the solidified first gel medium (lanes 1, 2, 5 and 6 of FIG. 6A) were less resolved than samples placed in regular agarose (lanes 3, 4, 7 and 8 of FIG. 6A).

EXAMPLE 2

Figure 7:
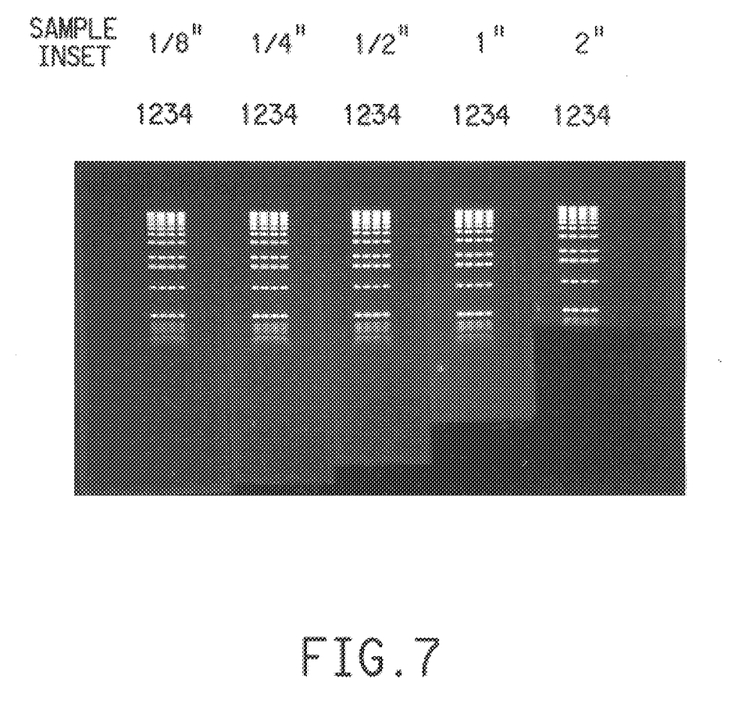
FIG. 7 is a photograph of the electrophoretic gel according to Example 2 of the present invention showing the bands resulting from the samples inset from the edge of the gel bed at ⅛", ¼", ½", 1" and 2". Lane 1 contained 0.750% agarose; lane 2—0.675% agarose; lane 3—0.600% agarose; and lane 4—0.525% agarose.

A set of DNA samples were prepared by adding DNA ("1 kb Ladder" from BRL, Inc., Gaithersberg, Md.) to molten agarose, as described in Example 1 to yield a final percent agarose concentration of 0.750, 0.675, 0.600 and 0.525 (see FIG. 7, lanes 1, 2, 3 and 4 respectively). Five different sets of samples were prepared and cast into a gel. The gel was sliced along the direction of electrophoresis into 5 pieces. Each piece was slid inward from the edge of the gel bed by distances of $\frac{1}{8}$", $\frac{1}{4}$", $\frac{1}{2}$", 1" or 2". Electrophoresis and visualization of the DNA samples was performed as described in Example 1.

As shown in FIG. 7, the resolution of each sample is essentially equivalent with sharp, slightly slanted bands. DNA samples set back from the edge of the gel bed by as little as $\frac{1}{8}$ were resolved well. The concentration of agarose in the solidified first gel medium had no observable effect on resolution of the DNA samples during electrophoresis. Low concentrations of agarose can therefore be used for the solidified first gel medium allowing more flexibility in sample preparation before the agarose solidifies.

EXAMPLE 3

Figure 8A:
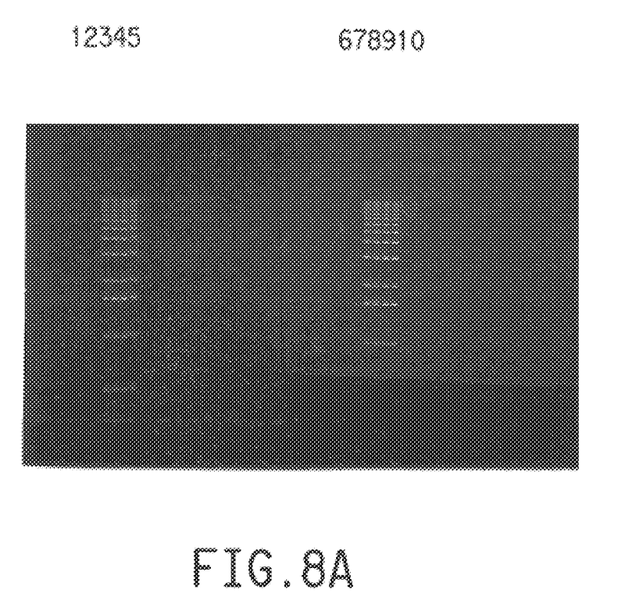
FIG. 8A is a photograph of the electrophoretic gel according to Example 3 of the present invention. Lanes 1–5 show the bands resulting from the samples inset ⅛" from the edge of the gel bed. Lanes 6–10 show the bands resulting from the samples inset 1" from the edge of the gel bed. Lanes 1 and 6 contained 0.50% agarose; lanes 2 and 7—0.45% agarose; lanes 3 and 8—0.40% agarose; lanes 4 and 9—0.35% agarose; and lanes 5 and 10—0.30% agarose.

Two sets of DNA samples ("1 kb Ladder" from BRL, Inc., Gaithersberg, Md.) were prepared and mixed with agarose as described in Example 1 to yield a final percent agarose concentration of 0.50, 0.45, 0.40, 0.35 and 0.30 (see FIG. 8A, lanes 1 and 6—0.50%; lanes 2 and 7—0.45%; lanes 3 and 8—0.40%; lanes 4 and 9—0.35%; and lanes 5 and 10—0.30%). The samples were placed in the sample holder and allowed to solidify at room temperature. Samples in 0.30% agarose failed to solidify in the sample holder, and were removed from the sample holder before pouring the solidified second gel medium (lanes 5 and 10).

Figure 8B:
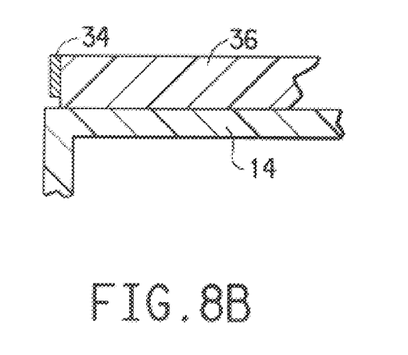
FIG. 8B is a cross-sectional view of the gel bed, the solidified second gel medium and the mixture of sample and first gel medium of Example 3 of the present invention showing the sample inset ⅛" from the edge of the gel bed.
Figure 8C:
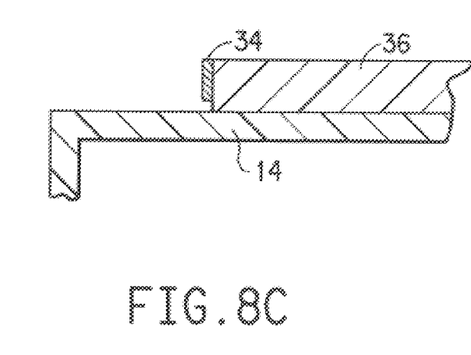
FIG. 8C is a cross-sectional view of the gel bed, the solidified second gel medium and the mixture of sample and first gel medium of Example 3 of the present invention showing the sample inset 1" from the edge of the gel bed.

The sample holder was shaped so as to inset the adhered samples just within the edge of the gel bed; the backside of the adhered sample was just flush with the edge of the gel bed, while the frontside of the adhered sample was inset ⅛ from the edge of the gel bed, as shown in FIG. 8B. The gel was sliced along the direction of electrophoresis into 2 halves. One half was slid inward 1" from the edge of the gel bed (FIG. 8C) and the other half was left in place (FIG. 8B). Electrophoresis and visualization of the DNA samples were performed as described in Example 1.

The results shown in FIG. 8A demonstrate that agarose concentration as low as 0.35% will function as the solidified second gel medium, and that DNA samples cast in place and set back from the edge of the gel bed at ⅛ (lanes 1–5) resolve as well as samples that are set back from the edge of the gel bed at 1" (lanes 6–10).

EXAMPLE 4

DNA samples were prepared by mixing 203 μl 10 mM Tris-HCl pH 7.5, 0.1 mM EDTA with 498 μl DNA ("1 kb Ladder" from BRL, Inc., Gaithersberg, Md.), and 378 μl of a 1% agarose solution and held at 55° C. Each of 76 sample wells in a sample holder were filled with 13 μl of the DNA/agarose solution and allowed to solidify at room temperature. The sample holder was assembled into the electrophoresis unit, a gel was cast on the gel bed with a 1% solution of agarose and allowed to solidify, and electrophoresis and DNA visualization were performed as described in Example 1.

Figure 9:
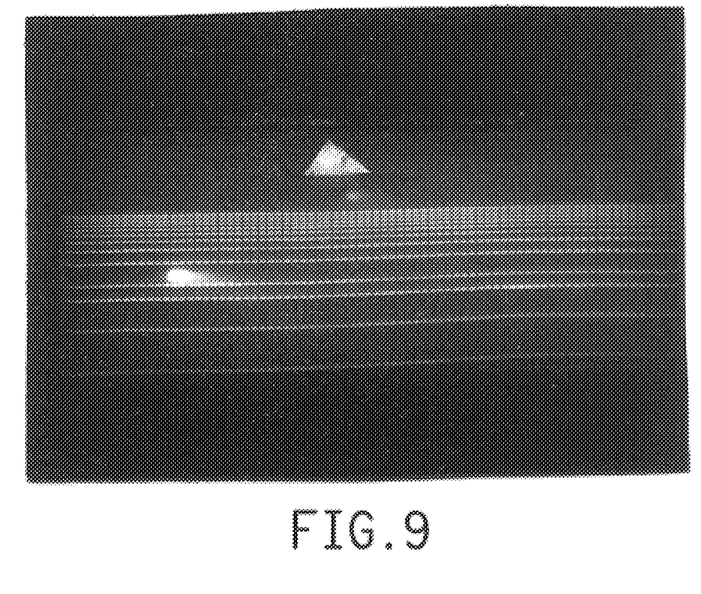
FIG. 9 is a photograph of the electrophoretic gel according to Example 4 of the present invention showing the bands of 76 DNA samples.

The results shown in FIG. 9 demonstrate that all 76 DNA samples were separated with high resolution.

What I claim is:

1. A sample holder for receiving a presolidified electrophoretic sample and for containing said electrophoretic gel sample after solidification for delivery to an electrophoretic gel, said sample holder comprising:
    a plate having a front face and a flat back face, said front face having at least one sample well therein, said sample well extending into said plate and terminating prior to said back face; and
    a backing for facilitating placement of the sample holder within an electrophoretic chamber in proximity to an electrophoretic gel bed, wherein said backing is attached to the back face of said plate, wherein said backing extends in a downward vertical direction beyond a bottom edge of the plate, and further wherein upon placement of said sample holder within the electrophoretic chamber of a horizontal electrophoretic unit said plate is positioned inset from an edge and over a top surface of the electrophoretic gel bed.

2. The sample holder as recited in claim 1, wherein said plate and said backing comprise one piece of material.

3. A sample holder as recited in claim 1, wherein the plate is substantially planar and rectangular and comprises a plurality of sample wells longitudinally aligned along the front face of said plate.

4. The sample holder as recited in claim 1, wherein said plate comprises material for facilitating removal of said sample holder from the solidified gel samples contained in the sample wells.

5. The sample holder as recited in claim 1, wherein said sample holder comprises an electrically conductive material.

6. A process for loading an electrophoretic gel sample onto an electrophoretic gel, comprising the steps of:
    (a) delivering the sample and a molten first gel medium to a sample well formed within a sample holder, said sample holder comprising:
        a plate having at least one sample well formed in the front face thereof;
    (b) allowing the sample and the molten first gel medium to solidify within the sample well;
    (c) positioning said sample holder in an electrophoretic chamber in a manner sufficient to place the solidified first gel medium contained in the sample well in proximity to a bed within the electrophoretic chamber;
    (d) adding a molten second gel medium onto the bed within the electrophoretic chamber so that the molten second gel medium is contacted with the solidified first gel medium contained in the sample well recited in step (c); and
    (e) allowing the molten second gel medium to solidify in the bed.

7. The process of claim 6, further comprising the step of:
    (a) removing said sample holder leaving the sample and first gel medium adhered to the solidified second gel medium, whereby the sample contained in the solidified first gel medium migrates to the solidified second gel medium when electrophoretic current is applied.

8. The process of claim 6, wherein said positioning step (c) places the sample and first gel medium in a position inset from the edge of the bed over the top surface of the bed.

9. The process of claim 6 wherein both the first and second gel medium are agarose and electrophoresis is performed in a horizontal electrophoresis unit.

10. The process of claim 6 wherein in step (a) the delivery of sample and molten first gel medium to the sample holder is accomplished using automatic means.

11. The process of claim 6, further comprising after step (b), storing the sample holder containing the solidified sample and first gel medium for a period prior to performing step (c).

12. An apparatus for performing gel electrophoresis, comprising:
    (a) an electrophoretic chamber having an electrophoretic bed, said bed being positioned between two buffer/electrode compartments and extending from one side wall of the electrophoretic chamber to an opposite side wall of the electrophoretic chamber;
    (b) a sample holder comprising a plate having a front face and a flat back face, said front face having a plurality of sample wells, said sample wells extending into said plate and terminating prior to said back face; and a backing for facilitating placement of the sample holder within an electrophoretic chamber in Proximity to an electrophoretic unit bed, wherein said backing is attached to the back face of said plate, and said backing extends in a downward vertical direction beyond a bottom edge of the plate, and further wherein upon placement of said sample holder within the electrophoretic chamber of a horizontal electrophoretic unit said plate is positioned inset from an edge and over a top surface of the electrophoretic gel bed; and
    (c) automatic means to deliver multiple electrophoretic samples and molten first gel medium to the sample wells of the sample holder prior to positioning said sample holder within said electrophoretic chamber.

13. The system as recited in claim 12 wherein in step (c) the first gel medium is agarose, and in step (a) further comprising a second gel medium made of agarose contained in the electrophoretic chamber on the surface of the bed.

14. A sample holder for receiving a pre-solidified electrophoretic sample and for containing said electrophoretic gel sample after solidification for delivery to an electrophoretic gel, said sample holder comprising:

a plate extending in a first plane and having a front face and a flat back face and a first side face and a second side face, said front face having at least one sample well therein extending generally perpendicular to the plane of the plate and proximate the first side face; and a backing for facilitating placement of the sample holder, wherein said backing is disposed in contact with said plate, said backing extending in a second plane generally parallel to the first plane of the plate and having a portion extending beyond the first side face of the plate.

15. The sample holder of claim 14, wherein the plate and the backing are one piece.

16. The sample holder of claim 14, wherein the plate and the backing are two separate pieces.

* * * * *